United States Patent [19]

Chippendale et al.

[11] Patent Number: 5,349,944
[45] Date of Patent: Sep. 27, 1994

[54] INHALATION DEVICES WITH A REDUCED RISK OF BLOCKAGE

[75] Inventors: Kevan E. Chippendale, Stoke on Trent; John S. Corbett, Loughborough; John L. Hart, Bramcote; Geraldine Walkley, Melton Mowbray, all of England

[73] Assignee: Fisons plc, Ipswich, England

[21] Appl. No.: 958,449

[22] Filed: Oct. 7, 1992

Related U.S. Application Data

[63] Continuation of Ser. No. 487,963, Jul. 5, 1990, abandoned.

[30] Foreign Application Priority Data

Mar. 28, 1988 [GB] United Kingdom ............... 8806990
Mar. 28, 1988 [GB] United Kingdom ............... 8806991
Aug. 9, 1988 [GB] United Kingdom ............... 8818180
Sep. 10, 1988 [GB] United Kingdom ............... 8821339

[51] Int. Cl.$^5$ ............................................. A61M 11/00
[52] U.S. Cl. ............................ 128/200.14; 128/200.23
[58] Field of Search ................... 128/200.14, 200.23, 128/203.12

[56] References Cited

U.S. PATENT DOCUMENTS

| | | | |
|---|---|---|---|
| 1,892,750 | 1/1933 | Rotheim | 128/200.23 |
| 3,739,950 | 6/1973 | Gorman | 128/200.23 |
| 3,994,421 | 11/1976 | Hansen | 128/200.23 |
| 4,052,985 | 10/1977 | Coleman et al. | 128/200.23 |
| 4,130,116 | 12/1978 | Cavazza | 128/200.23 |
| 4,796,614 | 1/1989 | Nowacki et al. | 128/200.23 |
| 4,940,051 | 7/1990 | Lankinen | 128/200.23 |
| 5,027,808 | 7/1991 | Rich et al. | 128/200.23 |
| 5,060,643 | 10/1991 | Rich et al. | 128/200.23 |
| 5,134,993 | 8/1992 | van der Linden et al. | 128/200.23 |

*Primary Examiner*—Edgar S. Burr
*Assistant Examiner*—Aaron J. Lewis
*Attorney, Agent, or Firm*—Marshall, O'Toole, Gerstein, Murray & Borun

[57] ABSTRACT

An aerosol inhalation device, having a mouthpiece (12) and a canister (15) of pressurized hygroscopic medicament, the canister (15) being fitted at one end with a dispensing metering valve; wherein a protective barrier (19) is provided between the dispensing metering valve and the mouthpiece (12) so as to eliminate or substantially reduce blockage of the device.

2 Claims, 4 Drawing Sheets

INHALATION DEVICES WITH A REDUCED RISK OF BLOCKAGE

This application is a continuation, of application Ser. No. 07/487,963, filed Jul. 5, 1990 now abandoned.

This invention relates to inhalation devices, more particularly to improved aerosol inhalation devices containing hygroscopic drugs.

The use of aerosol inhalation devices for the administration by inhalation of medicaments in the form of powder aerosols is well known. Such devices generally comprise a housing which receives a canister of pressurised medicament. The canister is provided with a dispensing metering valve including a metering chamber and a hollow valve stem which is sealed at one end. The sealed end of the valve stem is seated in the valve and the open end locates in a spray head within the housing.

Medicament is discharged by moving the canister relative to the valve stem. This changes the dispensing metering valve from an inoperative state in which the metering chamber is isolated from the atmosphere to an operative state in which the metering chamber communicates with the atmosphere via the valve stem and an outlet orifice provided in the spray head. Usually, the valve stem is provided close to its sealed end with a lateral inlet port. In the inoperative state the inlet port is located outside the valve; in the operative state it is within the metering chamber and medicament can pass from the chamber through the inlet port, the valve stem, the spray head and the outlet orifice into the housing from where it can be inhaled by a user inhaling at a mouthpiece formed in the housing.

A problem which can occur when devices of this type are used to administer hygroscopic medicaments is blockage.

We have now surprisingly found that blockage of inhalation devices used to administer hygroscopic medicaments can be eliminated or substantially mitigated by interposing a protective barrier between the dispensing metering valve and the mouthpiece.

Thus, according to the present invention there is provided an aerosol inhalation device, comprising a mouthpiece and a canister of pressurised hygroscopic medicament, the canister being fitted at one end with a dispensing metering valve; characterised in that a protective barrier is provided between the dispensing metering valve and the mouthpiece.

By "hygroscopic medicament" we mean a medicament which takes up significant amounts of water when in a moist atmosphere, for example one which at 90% relative humidity (being approximately a lower value for the relative humidity found in human breath) takes up more than 8% of its own weight of water. Examples of such medicaments include sodium cromoglycate and nedocromil sodium.

We have surprisingly found that the problem of blockage is especially well alleviated by shielding of the lateral inlet port of the valve stem, where such a port is present.

Thus, we particularly prefer the protective barrier to shield the inlet port from a user's breath and, in a first form of the present invention, there is provided an aerosol inhalation device in which the dispensing metering valve has a valve stem provided with an inlet port, and the barrier shields the inlet port from a user's breath.

The aerosol inhalation devices of the invention have the advantages that they do not become blocked or block less frequently, so that a canister of medicament can be exhausted without the danger of the device being discarded prematurely because the patient mistakenly believes that the canister is empty or because it cannot readily be unblocked; there is a greatly reduced risk of plugs of medicament forming in the devices which are subsequently inhaled by the patient—this is especially dangerous for patients who have breathing difficulties and who are most likely to be using aerosol inhalation devices: the devices are more hygienic because there are fewer or no medicament accretion surfaces which bacteria may colonize; and they need to be cleaned less frequently—cleaning being a difficult task for patients who have unsteady hands.

Suitable barriers for shielding the inlet port from a user's breath include a piece of open celled foam placed around the portion of the valve stem which includes the inlet port.

The piece of open celled foam may take the form of a washer applied to the outside of a conventional metering valve. In such a case, the washer is preferably retained by an overcap, e.g. of plastics material, fitting over the valve. Alternatively, the barrier may be integral with the valve, such that it can be incorporated within a ferrule for attachment to the pressurised medicament canister.

We prefer arrangements in which the barrier is able to brush the surface of the valve stem and thus help further prevent blockage and the build up of accretions of medicament. Thus, in a particularly preferred embodiment, the barrier is a cap, e.g. of elastomeric material, fitting over the end of the canister fitted with the valve and provided with a frusto-conical central portion defining an aperture through which the valve stem protrudes, the arrangement preferably being such that the cap brushes the surface of the valve stem.

When the barrier is a cap, the cap may be provided with means for engaging the aerosol inhalation device in which the pressurised medicament canister is to be used. The engaging means may be, for example, a keyway or recess formed on the cap which is adapted to receive a key or protrusion formed on the aerosol inhalation device. This has the advantage that a given inhalation device fitted with a key or protrusion may only be used with pressurised aerosol canisters fitted with a cap having a complementary keyway or recess, thereby improving hygiene, reducing medicament misuse, and reducing the risk of accidental administration of the wrong medicament. Of course, the opposite configuration may be envisaged in which the keyway or recess is formed on the aerosol inhalation device and the key or protrusion is formed on the cap.

In a second form of the invention, the barrier shields all or part of the valve stem from a user's breath. Thus, the barrier may extend from the spray head to at least the end of the canister fitted with the valve, or it may divide the housing into a canister containing portion and a spray head containing portion.

To facilitate inhalation by a patient, it is preferred that the barrier does not impair passage of air through the device. Thus, when the barrier extends from the spray head to at least the end of the canister fitted with the valve, there is preferably a clearance between the barrier and the walls of the housing; and when the barrier divides the housing into a canister containing portion and a spray head containing portion, there is preferably at least one air inlet provided in the spray head containing portion of the housing.

In a third form of the invention, the barrier is movable such that it shields the outlet orifice from a user's breath when the dispensing metering valve is in an inoperative state in which medicament is not released, and exposes the outlet orifice to the user when the dispensing metering valve is in an operative state in which medicament is released.

In this form of the invention, the barrier may move in response to movement of the canister, and may also be capable of limited movement relative to the canister. This is preferred where the range of motion by the barrier needed to expose the outlet orifice is greater than the range of motion needed to actuate the canister. Relative motion of the canister and barrier may be effected by the action of a spring biasing the barrier away from the canister. The spring may be independent, or may be an integral part of the barrier. The spring may be situated between the barrier and the canister, e.g. between the base of the canister and a cup provided on the protecting member, or it may be situated between the barrier and the spray head or the housing of the inhalation device.

Preferred embodiments of the present invention will now be described, by way of example, with reference to the accompanying drawings, in which.

In the Figures, corresponding components are given a similar reference numeral where this aids understanding.

Figure 1:
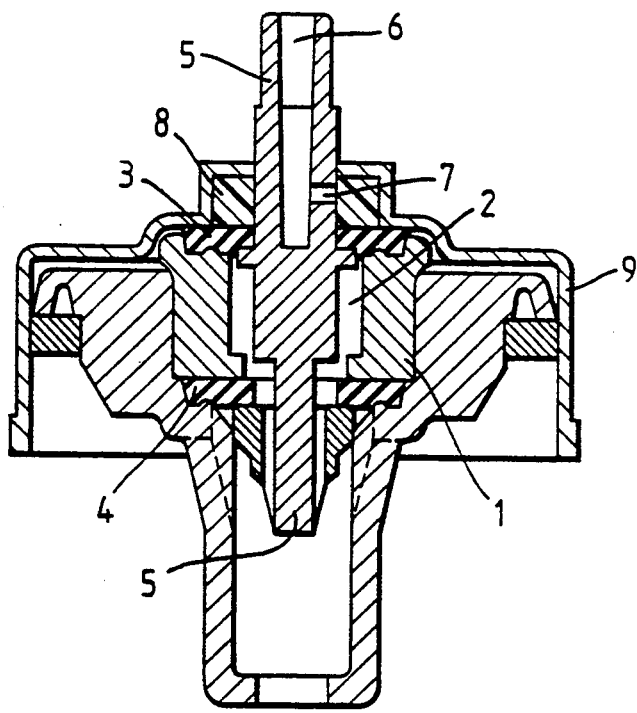
FIG. 1 is a vertical section through a dispensing metering valve of an aerosol inhalation device having a barrier to shield the lateral inlet port.

FIG. 1 shows a dispensing metering valve from a medicament canister. The dispensing metering valve comprises a valve body 1 which encloses a metering chamber 2 which is closed at its upper and lower ends by seals 3 and 4 respectively. A valve stem 5 is centrally disposed in the chamber 2 and cooperates with the seals 3 and 4. The valve stem 5 is provided with a disharge vent 6 along part of its long axis such that the end of the valve stem 5 remote from the valve is open, and a lateral inlet port 7 transverse to and communicating with the disharge vent 6. The valve stem 5 is movable axially, and its movement changes the valve from an inoperative state (illustrated) in which the chamber 2 is isolated from the atmosphere while the chamber communicates with the contents of the container, and an operative state in which the contents of the chamber 2 can be discharged to the atmosphere through the discharge vent 6 via the inlet port 7.

The inlet port 7 is protected from a user's breath, and cleaned by, a foam washer 8 which surrounds the portion of valve stem 5 including the inlet port 7. The valve is held onto the canister by means of a ferrule 9 which encloses the washer 8 as well as the valve body 1 and seals 3,4.

Figure 2:
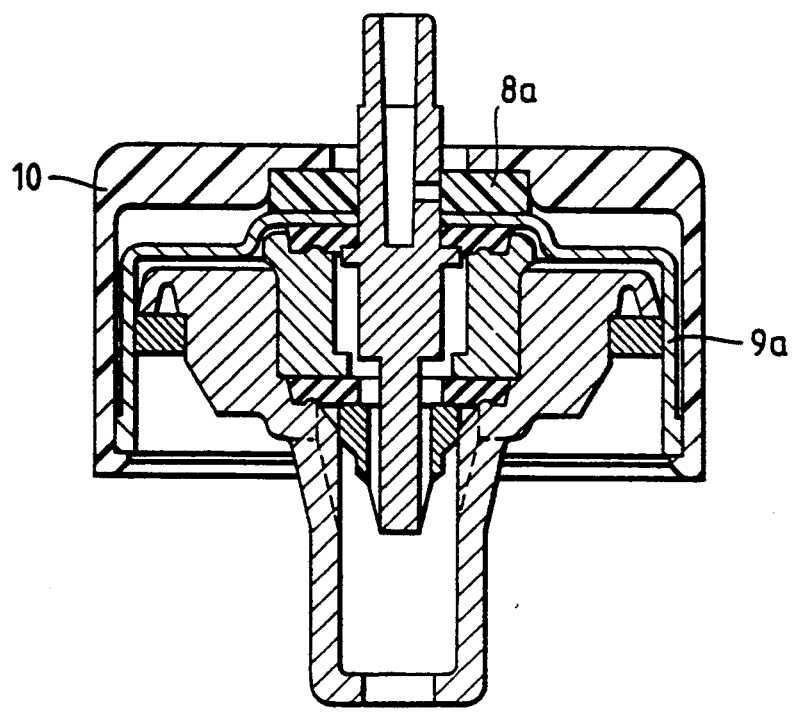
FIG. 2 shows the dispensing metering valve of FIG. 1 fitted with a different barrier.

The embodiment shown in FIG. 2 is similar to that described above except that the washer 8a is located outside the ferrule 9a and is retained in place by a plastics overcap 10 which has a snap-fit with the rim of the ferrule 9a.

Figure 3:
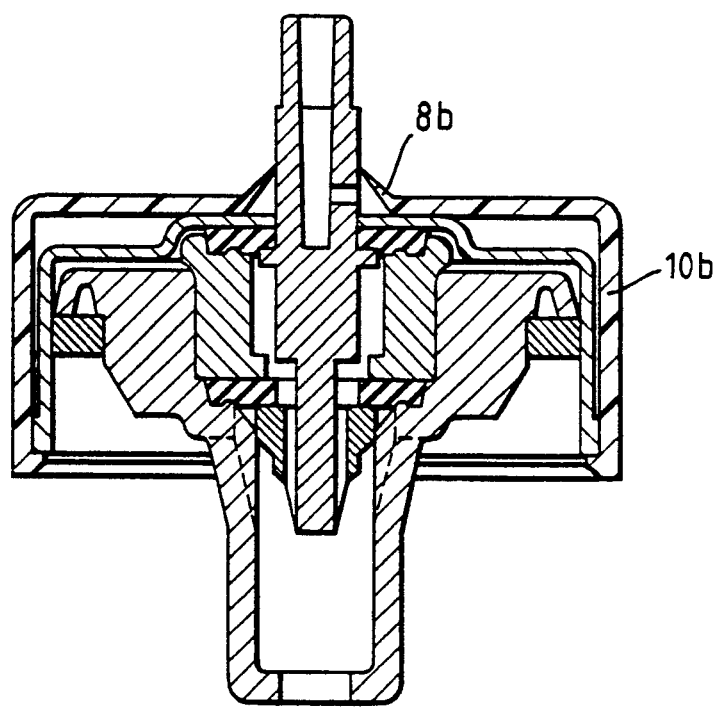
FIG. 3 shows the dispensing metering valve of FIG. 1 fitted with another different barrier.

The embodiment shown in FIG. 3 is similar to that of FIG. 2 with the exception that the washer 8a is replaced by a frusto-conical protrusion 8b in the cap 10b.

Figure 4:
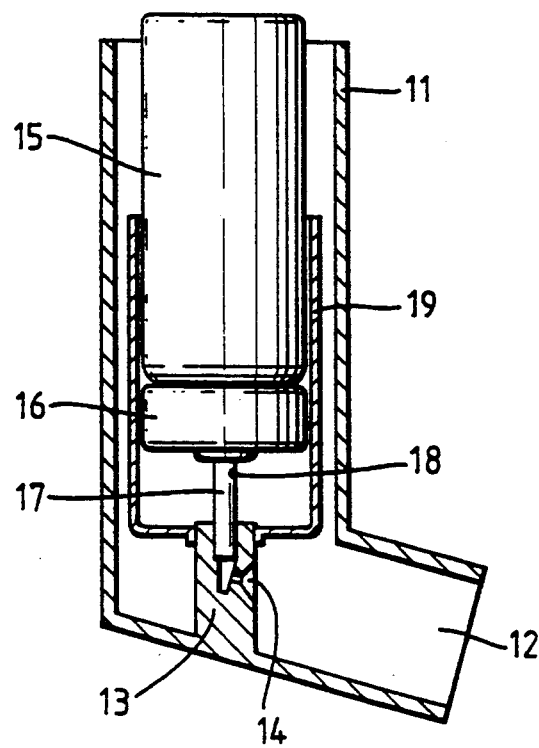
FIG. 4 is a side view in partial section of an inhalation device provided with a spray head to which is affixed a generally cylindrical barrier.

The device shown in FIG. 4 comprises a generally cylindrical housing 11 provided with an integrally moulded mouthpiece 12 and spray head 13 having an outlet orifice 14. Located within housing 11 is a canister 15 of pressurised hygroscopic medicament. Canister 15 is provided at one end with a dispensing metering valve (as described above) which is retained by an aluminium ferrule 16. Extending from the valve and seated in spray head 13 is a valve stem 17 (as described above) having an inlet port 18. A generally cylindrical barrier 19 is affixed to spray head 13 and extends along the length of canister 15, substantially surrounding the lower portion of the canister.

The device is shown with the valve in the inoperative state in which inlet port 18 is outside the metering valve. To dispense medicament, the valve is changed to an operative state by depressing canister 15 relative to valve stem 17. In the operative state, inlet port 18 is located within the metering chamber of the valve and the contents of the metering chamber pass via inlet port 18, valve stem 17 and outlet orifice 14 into mouthpiece 12 from where they can be inhaled by a user. Clearance between barrier 19 and the sides of housing 11 enables the passage of air through the device during inhalation. When the valve is in the inoperative state, inlet port 18 is protected from the user's moist breath by barrier 19.

Figure 5:
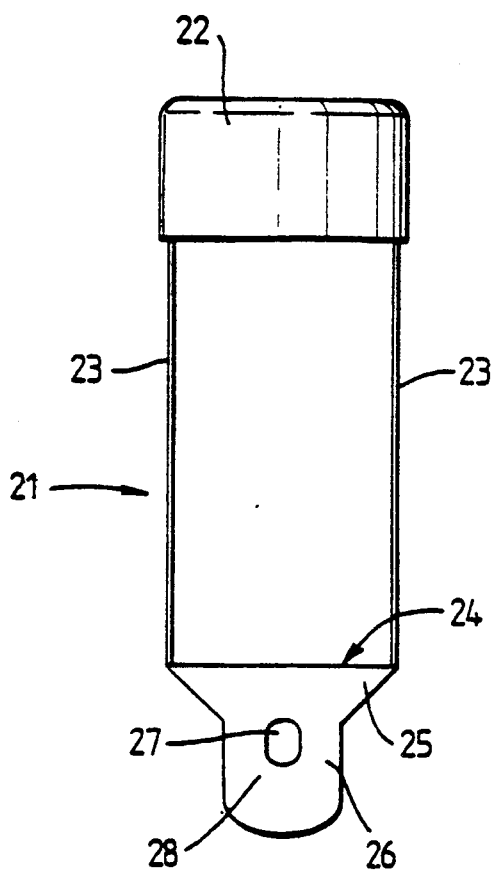
FIG. 5 is a front view of a movable barrier.

Referring now to FIG. 5, a barrier 21 comprises a cup 22 and two limbs 23 connecting the cup 22 to a body 24.

The body comprises a frusto-conical upper portion 25 and a generally cylindrical lower portion 26 which is truncated obliquely (see FIG. 6) and is provided with an opening 27 in its longest surface 28.

Figure 6:
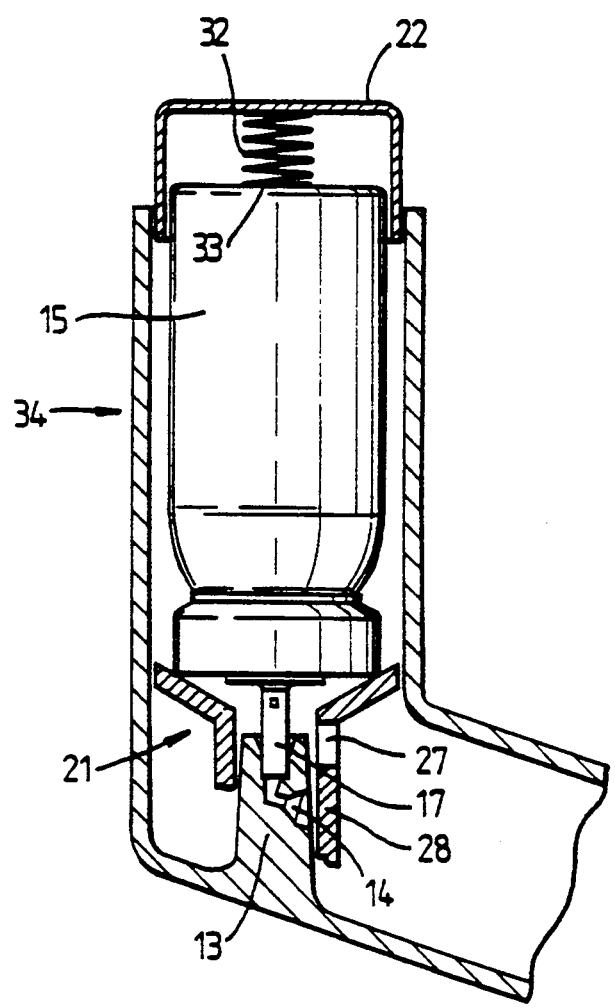
FIG. 6 is a side view in partial section of an inhalation device fitted with the barrier of FIG. 5.

FIG. 6 shows the barrier 21 in position in an aerosol inhalation device 34, which device comprises similar components to those shown in FIG. 4. The end of the canister fitted with the dispensing metering valve rests on the upper portion 25 of the body 24 of the barrier. The base of the canister 33 fits into the cup 22 of the barrier, and a compression spring 32 is situated between the base of the canister 33 and the cup 22.

When the valve is in the inoperative state (illustrated), barrier 21 is positioned over the outlet orifice 14 thus shielding it from a user's breath. In use, the patient urges cup 22 down towards the base of the canister against the bias of spring 32. This causes relative motion of barrier 21 and canister 15, both of which move downwards. Opening 27 is aligned with outlet orifice 14 at the same time as the valve is actuated, allowing medicament to be released via valve stem 17, spray head 13, spray orifice 14, opening 27 and mouthpiece 12 from where it is inhaled.

Figure 7:
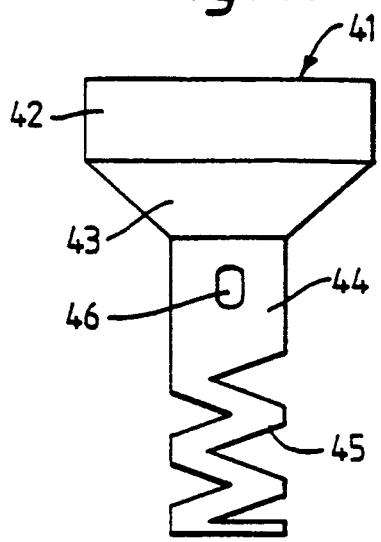
FIG. 7 is a front view of another movable barrier.

FIG. 7 shows a barrier 41 comprising a cylindrical upper portion 42, a frusto-conical middle portion 43, and a lower cylindrical portion 44 which is provided with an opening 46 and a spring shaped member 45.

Figure 8:
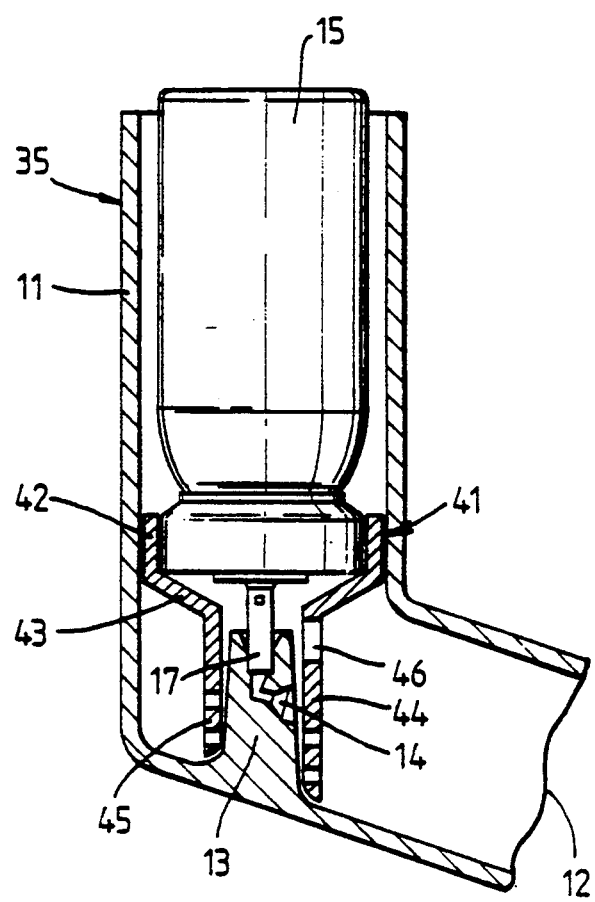
FIG. 8 is a side view in partial section of an inhalation device fitted with the barrier of FIG. 7.

FIG. 8 shows barrier 41 in position in an aerosol inhalation device 35, which device comprises similar components to those shown in FIGS. 4 and 6. The end of canister 15 fitted with the valve fits into the upper portion 42 of barrier 41 and abuts the frusto-conical portion 43. The spring portion 45 of barrier 41 rests on the inner surface of housing 11 and surrounds spray head 13, with opening 46 situated directly above outlet orifice 14.

When the valve is in the inoperative state, outlet orifice 14 is shielded from a user's breath by the lower cylindrical portion 44 of barrier 41. In use, the patient depresses the canister leading to compression of spring portion 45, and relative movement of barrier 41 and canister 15, such that opening 46 is aligned with outlet orifice 14 when the valve is in the operative state.

Figure 9:
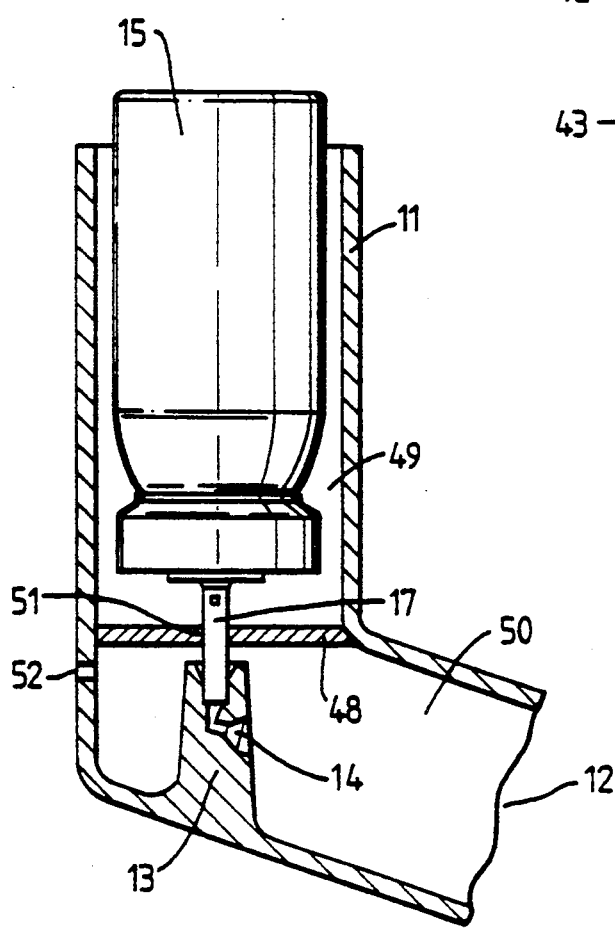
FIG. 9 is a side view in partial section of an inhalation device provided with a housing in which the barrier divides the housing into a spray head containing portion and a canister containing portion.

FIG. 9 shows a device resembling that shown in FIG. 4. A barrier 48 divides housing 11 into a canister containing portion 49 and a spray head containing portion 50 and is provided with a closely fitting opening 51 through which valve stem 17 passes. At least one air inlet 52 is provided behind the spray head. The barrier 48 thus shields the dispensing metering valve from a user's breath during use.

We claim:

1. An aerosol inhalation device, comprising:
   a mouthpiece;
   a canister of pressurized hygroscopic medicament, said canister having an end fitted with a dispensing metering valve feeding said medicament to said mouthpiece, said metering valve having a valve stem provided with an inlet port;
   said valve stem being movable between an inoperative position in which the inlet port is located outside the metering valve and an operative state in which the inlet port is located within the metering valve; and
   a cap of elastomeric material fitted over the end of the canister provided with the valve, said cap being provided with a frusto-conical central portion through which the valve stem passes and protrudes, such that in the inoperative position of the valve stem, the cap shields the inlet port from a user's breath and upon movement between the inoperative and operative positions the cap brushes the surface of the valve stem.

2. An aerosol inhalation device according to claim 1, wherein the medicament is sodium cromoglycate or nedocromil sodium.

* * * * *